United States Patent
Edgett et al.

(10) Patent No.: US 9,107,775 B2
(45) Date of Patent: Aug. 18, 2015

(54) TAMPON PLEDGET WITH IMPROVED BY-PASS LEAKAGE PROTECTION

(75) Inventors: Keith J. Edgett, Middletown, DE (US); Robert T. Jorgensen, Jr., Middletown, DE (US); Frank Glaug, Chester Springs, PA (US); Eugene P. Dougherty, Jr., Camden-Wyoming, DE (US)

(73) Assignee: Eveready Battery Company, Inc., St. Louis, MO (US)

( * ) Notice: Subject to any disclaimer, the term of this patent is extended or adjusted under 35 U.S.C. 154(b) by 478 days.

(21) Appl. No.: 12/424,018

(22) Filed: Apr. 15, 2009

(65) Prior Publication Data

US 2010/0268182 A1    Oct. 21, 2010

(51) Int. Cl.
*A61F 13/20* (2006.01)

(52) U.S. Cl.
CPC ......... *A61F 13/2085* (2013.01); *A61F 13/2051* (2013.01); *A61F 13/2054* (2013.01); *A61F 13/2068* (2013.01); *A61F 13/2088* (2013.01)

(58) Field of Classification Search
CPC ............ A61F 13/2051; A61F 13/2054; A61F 13/2068; A61F 13/2085; A61F 13/2088
USPC ............................. 604/379–380, 385.18, 904
See application file for complete search history.

(56) References Cited

U.S. PATENT DOCUMENTS

| | | |
|---|---|---|
| 1,401,358 A | 12/1921 | Peterkin |
| 2,391,343 A | 12/1945 | Popper |
| 2,412,861 A * | 12/1946 | George et al. ................. 604/379 |
| 2,499,414 A | 3/1950 | Rabell |
| 3,051,177 A | 8/1962 | Wilson |
| 3,079,921 A | 3/1963 | Brecht et al. |
| 3,340,874 A | 9/1967 | Burgeni |
| 3,371,666 A | 3/1968 | Lewing |

(Continued)

FOREIGN PATENT DOCUMENTS

| | | |
|---|---|---|
| BE | 768046 A | 11/1971 |
| CA | 2127144 A1 | 10/1995 |

(Continued)

OTHER PUBLICATIONS

International Search Report for PCT/US2010/030351 dated Jun. 3, 2010.

(Continued)

*Primary Examiner* — Lynne Anderson
(74) *Attorney, Agent, or Firm* — Edgewell Personal Care Brands, LLC (57) ABSTRACT

A tampon pledget is made by assembling one or more pads in a pad compression configuration, radially compressing the pad compression configuration in a traverse direction into a cylindrical form, and axially compressing the cylindrical form in a direction along a vertical axis to form the tampon pledget. In one embodiment, the axial compression is performed as a pressure is applied to at least one of a first and a second end of the cylindrical form. In one aspect of the present invention, the formed tampon pledget has an absorbent capacity as measured by the syngyna test of between about 6.0 grams to 9.0 grams and a density of about 0.4603 grams/cubic centimeter. In another aspect of the invention, the formed tampon pledget has an absorbent capacity as measured by the syngyna test of between about 9.0 grams to 12.0 grams and a density of about 0.4755 grams/cubic centimeter.

24 Claims, 6 Drawing Sheets

(56) References Cited

U.S. PATENT DOCUMENTS

| | | | |
|---|---|---|---|
| 3,572,341 A | 3/1971 | Glassman | |
| 3,610,243 A | 10/1971 | Jones, Sr. | |
| 3,618,605 A | 11/1971 | Glassman | |
| 3,628,534 A | 12/1971 | Donohue | |
| 3,643,661 A | 2/1972 | Crockford | |
| 3,683,912 A | 8/1972 | Olson et al. | |
| 3,695,270 A | 10/1972 | Dostal | |
| 3,731,687 A | 5/1973 | Glassman | |
| RE27,677 E | 6/1973 | Glassman | |
| 3,738,364 A | 6/1973 | Brien et al. | |
| 3,749,094 A | 7/1973 | Duncan | |
| 3,811,445 A * | 5/1974 | Dostal | 604/375 |
| 3,834,389 A | 9/1974 | Dulle | |
| 3,981,305 A * | 9/1976 | Ring | 604/15 |
| 4,200,101 A | 4/1980 | Glassman | |
| 4,274,412 A | 6/1981 | Austin | |
| 4,318,407 A | 3/1982 | Woon | |
| 4,335,720 A | 6/1982 | Glassman | |
| 4,335,721 A | 6/1982 | Matthews | |
| 4,374,522 A | 2/1983 | Olevsky | |
| 4,543,098 A | 9/1985 | Wolfe et al. | |
| 4,627,849 A | 12/1986 | Walton et al. | |
| 5,004,467 A | 4/1991 | Hinzmann et al. | |
| 5,006,116 A | 4/1991 | Alikhan et al. | |
| 5,047,024 A | 9/1991 | Glassman | |
| 5,153,971 A | 10/1992 | Iten | |
| 5,314,743 A | 5/1994 | Meirowitz et al. | |
| 5,659,934 A | 8/1997 | Jessup et al. | |
| 5,795,346 A | 8/1998 | Achter et al. | |
| 5,807,372 A | 9/1998 | Balzar | |
| 5,827,256 A | 10/1998 | Balzar | |
| 5,873,971 A | 2/1999 | Balzar | |
| 6,039,716 A * | 3/2000 | Jessup et al. | 604/385.18 |
| 6,177,608 B1 | 1/2001 | Weinstrauch | |
| 6,333,108 B1 * | 12/2001 | Wilkes et al. | 428/393 |
| 6,558,370 B2 * | 5/2003 | Moser | 604/317 |
| 6,585,300 B1 | 7/2003 | Rajala et al. | |
| 6,682,513 B2 * | 1/2004 | Agyapong et al. | 604/385.18 |
| 6,953,456 B2 * | 10/2005 | Fuchs et al. | 604/385.17 |
| 2002/0120243 A1 * | 8/2002 | Kraemer et al. | 604/367 |
| 2002/0156442 A1 | 10/2002 | Jackson et al. | |
| 2003/0131456 A1 | 7/2003 | Rajala et al. | |
| 2003/0208180 A1 * | 11/2003 | Fuchs et al. | 604/385.17 |
| 2003/0225389 A1 | 12/2003 | Cassoni et al. | |
| 2004/0019317 A1 * | 1/2004 | Takagi et al. | 604/11 |
| 2004/0126555 A1 | 7/2004 | Hartmann et al. | |
| 2005/0059944 A1 | 3/2005 | Jackson et al. | |
| 2007/0260211 A1 * | 11/2007 | Schmidt-Forst | 604/385.17 |
| 2008/0065041 A1 * | 3/2008 | Stan et al. | 604/385.18 |
| 2008/0097366 A1 * | 4/2008 | Mathews | 604/385.18 |
| 2008/0110005 A1 | 5/2008 | Gilbert et al. | |
| 2008/0119811 A1 * | 5/2008 | Gilbert et al. | 604/385.17 |
| 2008/0262464 A1 | 10/2008 | Hasse et al. | |
| 2008/0287902 A1 | 11/2008 | Edgett et al. | |
| 2009/0036859 A1 * | 2/2009 | Dougherty, Jr. et al. | 604/385.18 |
| 2009/0082712 A1 | 3/2009 | Hasse et al. | |
| 2010/0056981 A1 * | 3/2010 | Karapasha et al. | 604/11 |

FOREIGN PATENT DOCUMENTS

| | | |
|---|---|---|
| CA | 2180789 A1 | 1/1997 |
| CA | 2312666 A1 | 1/2001 |
| FR | 2505176 A | 11/1982 |
| GB | 1108197 A | 4/1968 |
| GB | 9306074 A | 5/1993 |
| IE | 8904080 A | 6/1990 |
| IL | 109027 | 6/1994 |
| JP | SHO44004240 | 2/1944 |
| WO | 9933428 A1 | 7/1999 |
| WO | 0006071 A1 | 2/2000 |
| WO | 0124729 A2 | 4/2001 |
| WO | 0166055 A1 | 9/2001 |
| WO | 02058587 A2 | 8/2002 |
| WO | 2005041833 A1 | 5/2005 |
| WO | 2008056339 A1 | 5/2008 |
| WO | 2008057581 A1 | 5/2008 |
| WO | 2008096331 A1 | 8/2008 |
| WO | 2008144624 A1 | 11/2008 |
| ZA | 8803191 A | 11/1988 |
| ZA | 9706745 A | 2/1998 |

OTHER PUBLICATIONS

Examination Report for corresponding GB Application No. GB1117582.5, Date of Report Mar. 27, 2013, pp. 1-2.

English Translation of Decision of Rejection against Japanese Patent Application No. 2012-506079; Date Mailed Jan. 7, 2013; pp. 1-4.

* cited by examiner

TAMPON PLEDGET WITH IMPROVED BY-PASS LEAKAGE PROTECTION

BACKGROUND OF THE INVENTION

1. Field of the Invention

This invention is directed to tampon pledgets and, more particularly, to tampon pledgets having improved absorbency and expansion characteristics to provide improved by-pass leakage protection.

2. Description of the Related Art

Absorbent catamenial tampons have long been known in the art. Most currently available tampon pledgets are compressed into a substantially cylindrical form from a generally rectangular pad of absorbent material, or a mix of absorbent and non-absorbent material. In use, the tampon pledget is inserted into a vagina of a female. As blood or other body fluids contacts the compressed tampon pledget, the fluid is absorbed and the pledget re-expands toward its pre-compressed size to capture the fluid that otherwise would flow from the vagina during menstruation. One key measure of tampon pledget performance is leakage protection. Most leakage is attributed to a "by-pass" of menstrual fluid. By-pass occurs when the menses travels along the length of the vaginal cavity without contacting the tampon pledget inserted therein. Tampon leakage typically ranges from about fifteen percent to twenty percent (15% to 20%) incidence of tampon leakage for all sizes (e.g., absorbency) of tampons.

The inventors have found that such by-pass is generally due to a less-than-optimal fit of the tampon pledget within the vagina cavity. The propensity of any commercially-produced tampon to leak is highly unpredictable due to, for example, differing manufacturing processes for fabricating tampons as a mass-marketed product and to wide anatomical variations in the vaginal cavity of women using the tampons. Both magnetic resonance imaging (MRI) analysis of actual users as well as ION simulations (anthropometrically correct simulation devices) indicate that a higher likelihood of by-pass leakage exists when the tampon pledget is inserted too high into the vaginal cavity and angled to either the right or left side of the fornices of the vagina. For example, in analyzing the MRI and ION simulation results the inventors have discovered that high placement of the tampon pledget within the vaginal cavity typically causes menstrual fluid from the cervical os (e.g., location where the menstrual fluid exits the uterus) to contact the inserted tampon pledget at approximately a mid or half-way point of a total length of the tampon pledget. As should be appreciated, it is generally preferred that the menstrual fluid contact the tampon pledget at top portion of the pledget's total length to maximize absorbency. As such, contacting the tampon pledget at the mid or half-way point causes the tampon pledget to absorb menstrual fluid less efficiently. For example, some MRI tests have shown that when placed relatively high in the vaginal cavity only a bottom portion of the tampon pledget absorbs fluid while a top portion of the tampon pledget remains relatively unsaturated. The inventors have observed this less than preferred absorption especially pronounced during "light flow" days of the menstrual cycle of female subjects.

As noted above, tampon pledgets are typically compressed and set either during manufacture or placement of the tampon pledget within an applicator barrel. When exposed to moisture and fluids within the body of a user (e.g., menstrual fluid), fibers of the tampon pledget expand. Conventional tampon pledget designs attempt to control expansion such that the expanding tampon pledget conforms to contours of the wearer's body. For example, it is typically a goal that the expansion significantly conform to a portion of the vaginal cavity to prevent by-pass leakage in pathways around the expanding tampon pledget. To date, efforts to control by-pass leakage have been somewhat successful. However, improvement in by-pass leakage protection is still desired. For example, the inventors have realized that since the vaginal cavity has greater elasticity than conventional tampon pledgets, the pledget tends to open up or stretch the width of the vaginal cavity contributing to the formation of by-pass leakage channels.

Given the above-described problems with conventional tampon pledgets, it is contemplated that users would prefer tampon products with improved expansion and absorption capabilities to substantially minimize, if not avoid, by-pass leakage. Accordingly, it has been discovered that there is a continuing need for an improved tampon pledget design and, in particular, for a tampon pledget design that has greater absorbency and expansion capabilities particularly in a radial direction.

SUMMARY OF THE INVENTION

In one aspect, the present invention resides in a method for making a tampon pledget including assembling at least two pads in a pad lay-up configuration, radially compressing the pad lay-up configuration in a traverse direction into a cylindrical form, and axially compressing the cylindrical form in a direction along a vertical axis to form the tampon pledget. In one embodiment, the formed tampon pledget has a density of about 0.42 grams/cubic centimeter and greater.

In one embodiment, the step of axial compression is comprised of axially compressing the cylindrical form as a pressure is applied to at least one of a first and a second end of the cylindrical form. In another embodiment, the axial compression is performed as a pressure is applied to both of the first and the second ends of the cylindrical form.

In one aspect of the present invention, the formed tampon pledget has an absorbent capacity as measured by the syngyna test of between about 6.0 grams to 9.0 grams and a density of about 0.4603 grams/cubic centimeter. In another aspect of the invention, the formed tampon pledget has an absorbent capacity as measured by the syngyna test of between about 9.0 grams to 12.0 grams and a density of about 0.4755 grams/cubic centimeter.

In one embodiment, the formed tampon pledget has an absorbent capacity as measured by the syngyna test of between about 6.0 grams to 9.0 grams, and at least one of a maximum displacement volume of about 3.00 milliliters and greater, and a rate of displacement of about 0.55 milliliters per minute and greater. In another embodiment, the formed tampon pledget has an absorbent capacity as measured by the syngyna test of between about 9.0 grams to 12.0 grams, a density of about 0.44 grams/cubic centimeter and greater, and at least one of a maximum displacement volume of about 4.20 milliliters and greater, a rate of displacement of at least about 0.65 milliliters per minute and greater, and a widthwise expansion of at least about 75% greater than its initial width prior to expansion, as compared to about 60% for conventional tampons.

In one aspect of the present invention a tampon pledget includes at least one pad which has been radially and axially compressed into a generally cylindrical form. After compression, the cylindrical form has a density of about 0.42 grams/cubic centimeter and greater. In one embodiment, cylindrical form further has an absorbent capacity as measured by the syngyna test of between about 6.0 grams to 9.0 grams, and a density of about 0.4603 grams/cubic centimeter. In another embodiment, the cylindrical form further has an absorbent capacity as measured by the syngyna test of between about 9.0 grams to 12.0 grams, and a density of about 0.4755 grams/cubic centimeter.

In one embodiment, the tampon pledget further includes a leak shield covering at least a portion of the tampon pledget. The leak shield has a second absorbency that is less than the absorbency of the tampon pledget. In one embodiment, the leak shield is comprised of a non-woven material that directs fluid to the tampon pledget when the tampon pledget is inserted in the vaginal cavity of a wearer.

DETAILED DESCRIPTION OF THE PREFERRED EMBODIMENTS

In one aspect of the present invention, a tampon pledget is provided that reduces by-pass leakage through an increase in pledget blooming or expansion capability. In one embodiment, the inventive tampon pledget provides increased expansion in its width to substantially conform to a width of a vaginal cavity of a wearer. The inventors have discovered that a tampon pledget that is highly compressed in both the radial and axial directions achieves a preferred, maximum blooming. In one embodiment, the high compression includes first compressing the tampon pledget in a radial direction and then compressing the tampon pledget in the axial direction. By axially compressing the pledget, the rayon fibers are forced towards a middle section of the tampon pledget, from both top and bottom sections of the pledget. The inventors have discovered that this two-step compressing process maximizes an amount of fiber (e.g., rayon fiber) per unit volume, which in turn creates a tampon pledget that blooms wider in a radial direction when it absorbs fluid. Additionally, the inventors have discovered that the inventive tampon pledget design produces a tampon pledget having a significantly higher density versus conventional tampon pledgets. The higher density is seen to provide more significant blooming as the tampon pledget contacts fluid. In one embodiment, the inventive tampon pledget includes an anti-leak shield, as described herein, to even further protect against by-pass leakage. As is described herein, the anti-leak shield prevents fluid from traveling past the highly compressed tampon pledget before the pledget has a chance to bloom to its maximum width by at least directing the fluid back toward the expanding tampon pledget.

Figure 1:
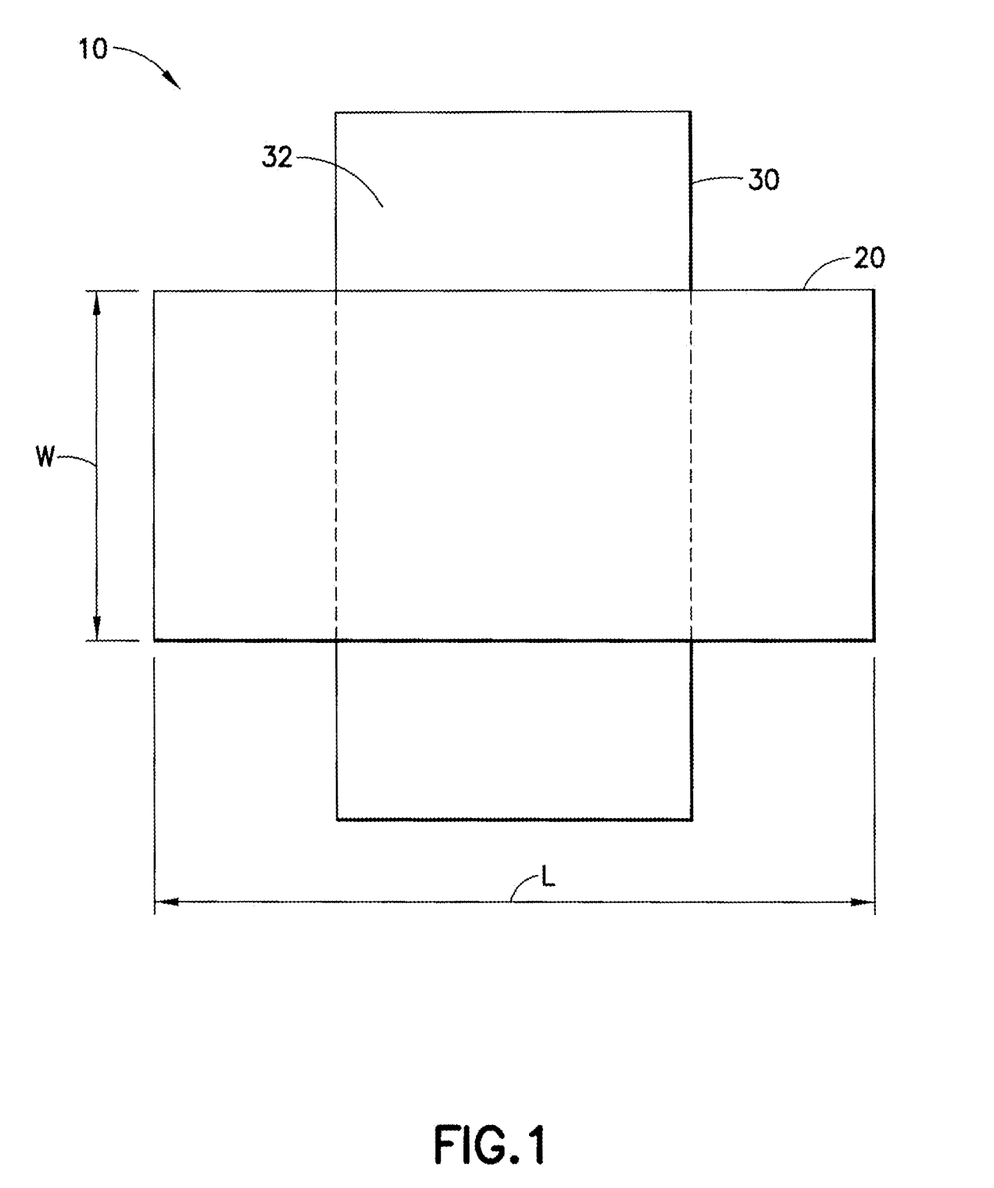
FIG. 1 is a plan view of pads positioned prior to formation of a tampon pledget in accordance with one embodiment of the present invention.

FIG. 1 illustrates a pad lay-up 10 including two webs of fiber such as, for example, cotton, rayon or other natural or synthetic fiber, cut into pads 20 and 30 having a predetermined width W and length L. In one embodiment, prior to assembly in the lay-up configuration, the webs are previously carded and needle punched and the predetermined width W and length L are about two inches (2.00 in.) and about four inches (4.00 in.), respectively. It should be appreciated that while the pads 20 and 30 are described as being similarly configured (e.g., having a same width and length dimension), it is within the scope of the present invention to provide pads having differing width and/or length dimensions, and/or geometrical shapes. As shown in FIG. 1, in a tampon pledget forming process the pad lay-up assembly 10 includes the pad 20 placed perpendicularly on a top surface 32 of the pad 30, creating a cross pattern. It should be appreciated that while two pads (e.g., pads 20 and 30) are shown, it is within the scope of the present invention to assembly two or more top pads layered on two or more bottom pads.

Figure 2:
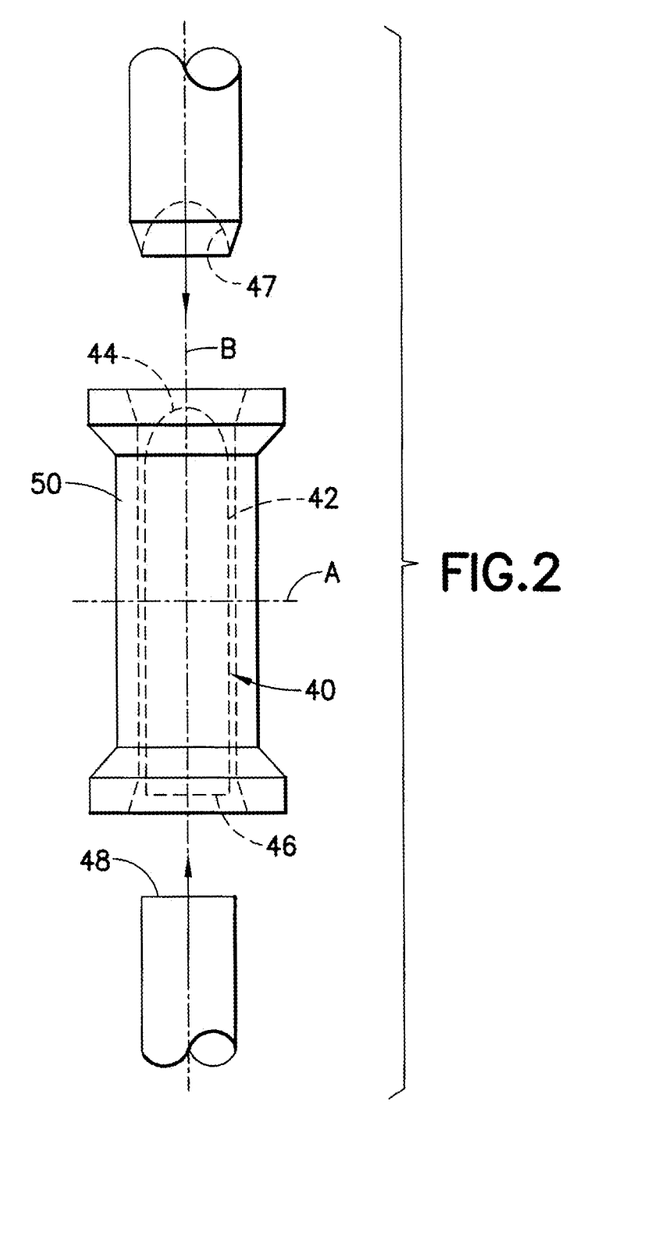
FIG. 2 is a plan view of an oven tube receiving the pads during a formation step of the tampon pledget, in accordance with the present invention.

The pad lay-up 10 is then compressed by, for example, ramming the pads 20 and 30 into a heated oven tube 50 (FIG. 2) such that the fibers of the pads 20 and 30 are radially compressed in a transverse or width direction along axis A into a generally cylindrical form 40. In one embodiment, an inside diameter of the oven tube 50 is about 0.407 in. for a Super Absorbency type tampon, and a target heating temperature is about two hundred thirty degrees Fahrenheit (230° F.). In one embodiment, the cylindrical form 40 is radially compressed in the oven tube 50 at an outer circumference 42 of the form 40 along axis A. In accordance with one aspect of the invention, the cylindrical form 40 is then axially compressed in the oven tube 50 in a direction along a vertical axis B. In one embodiment, the form 40 is axially compressed as pressure is applied at a top end 44 and a bottom end 46 of the cylindrical form 40. In one embodiment, the top end 44 is axially compressed with a conical/semi-circle shaped ram 47 and the bottom end 46 is axially compressed with a flat shaped ram 48. In one embodiment, axial compression of the ends 44 and 46 is performed at a temperature of about three hundred eighty-five degrees Fahrenheit (385° F.) for a dwell time of about twelve seconds (12 sec). The step of axial compression provides a tampon pledget (cylindrical form 40) that is of a relatively high density when compared to the density of conventional tampon pledgets. Axial compression under pressure is seen to further increase the density in the cylindrical form 40. For example, Table 1 illustrates the density of the inventive tampon pledget 40 (labeled "Pledget X" in Table 1) as compared to a GENTLE GLIDE® tampon product of Playtex Products, Inc. (Westport, Conn., USA), a BEYOND® tampon product of Playtex Products, Inc., and tampon products sold under the brand names TAMPAX ORIGINALS and PEARL (GENTLE GLIDE and BEYOND are registered trademarks of Playtex Products, Inc.). The data in Table 1 demonstrates a comparison of tampon pledget densities in grams per cubic centimeters (gms/cc) for "regular" and "super" tampon absorbencies as described in U.S. Food and Drug Administration regulations (21 CFR 801.430). The inventive tampon pledget 40 (Pledget X) demonstrates a higher density than conventional tampon pledgets. For example, in one embodiment, the density of inventive tampon pledgets is increased in a range of about twenty-five to fifty percent (25-50%) over conventional tampon pledgets, with a minimum increase in density of about ten percent (10%) and a maximum increase in density of about one hundred percent (100%).

TABLE 1

Tampon Density Comparison

| Product | Computed Pledget Densities (gms/cc) | |
| --- | --- | --- |
| | Regular | Super |
| GENTLE GLIDE | 0.3120 | 0.3829 |
| BEYOND | 0.4070 | 0.3468 |
| Pledget X | 0.4603 | 0.4755 |
| TAMPAX ORIGINALS | 0.3302 | 0.3522 |
| PEARL | 0.4061 | 0.3586 |

Figure 3:
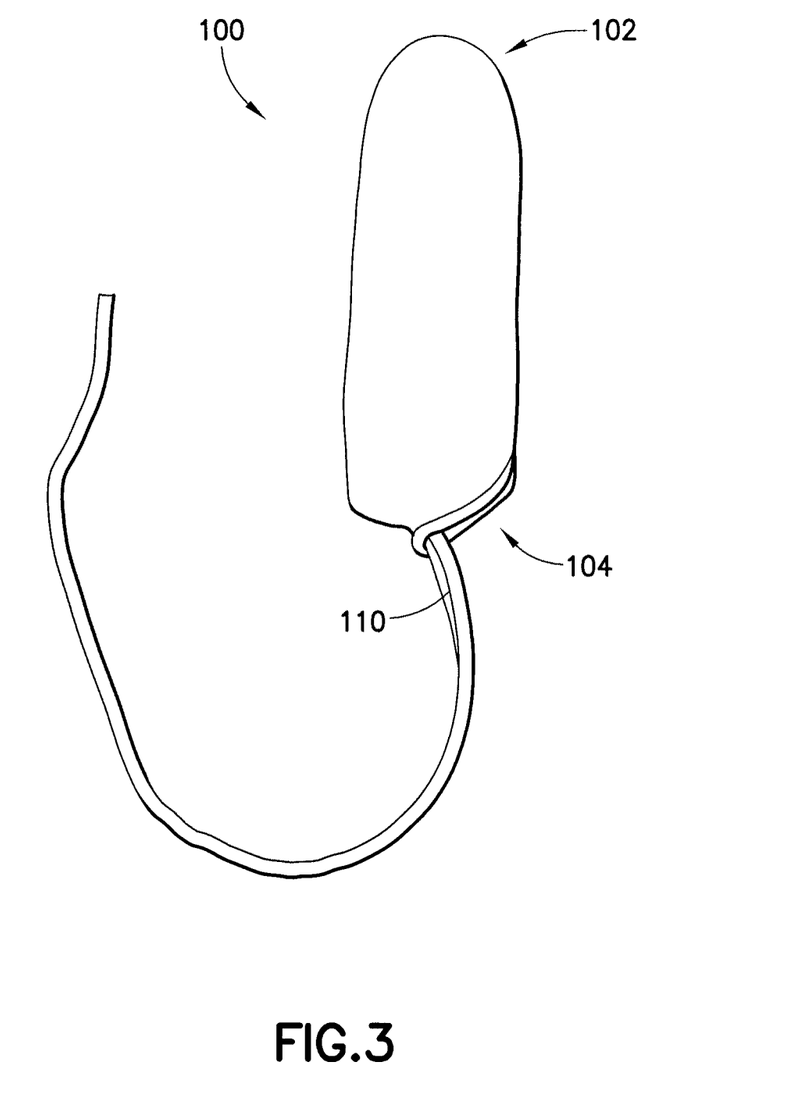
FIG. 3 is a plan view of a formed tampon pledget in accordance with one embodiment of the present invention.

It should be appreciated that while the tampon pledget 40 is depicted in a cylindrical form having one or more blunt ends, the inventive tampon pledget may be formed in any geometric shape. For example, the compressed tampon pledget 40 may include two flat or blunt ends, one blunt end and one geometrically shaped end, and two geometrically shaped ends. In one embodiment, the geometric shape may include, for example, a semi-circle, conical, taper, oval, inverted semi-circle, inverted conical, inverted taper, inverted oval, and the like. FIG. 3 illustrates one embodiment of the inventive tampon pledget, shown generally as a tampon pledget 100. As shown in FIG. 3, the tampon pledget 100 includes a first shaped end 102 in, for example, a semi-circular geometric shape and a second flat end 104. In one embodiment, the first end 102 of the pledget 100 is an insertion end and the second end 104 is a removal end. In one embodiment, illustrated in FIG. 3, the removal end 104 includes a withdrawal cord 110 to facilitate removal of the tampon pledget 100 from the vagina of a wearer.

Further comparison between the inventive tampon pledget 100 and conventional tampon pledgets were conducted using a modified syngyna absorbency test known a Positive Displacement Test. The Positive Displacement Test illustrates how rapidly a volume of a tampon pledget expands during a syngyna absorption test and, in particular, measures a maximum displacement volume (milliliters) associated with pledget expansion as it absorbs fluid. In one embodiment of the present invention, the maximum displacement volume (ml) is measured and recorded at predetermined time periods until a tampon pledget leaks. As should be appreciated, the measurements at predetermined time periods permit a calculation of a rate of displacement (ml/min). Tables 2-4 illustrate the results of the Positive Displacement Test, namely a Maximum Displacement (Table 2), Displacement Rates (Table 3) and Pledget Weights (Table 4) of the inventive tampon pledget 100 (again labeled "Pledget X" in Tables 2-4) as compared to a number of GENTLE GLIDE tampon and BEYOND tampon products of Playtex Products, Inc., and tampon products sold under the brand names TAMPAX ORIGINALS, PEARL, KOTEX, OB and LIL-LITES.

TABLE 2

Maximum Displacement.
Maximum Displacement (milliliters)

| Product Brand | Absorbency | |
| --- | --- | --- |
| | Regular | Super |
| GENTLE GLIDE | 1.60 | 3.07 |
| GENTLE GLIDE 2 | 1.98 | 3.60 |
| GENTLE GLIDE Odor Absorbent | 1.86 | 3.64 |
| BEYOND | 1.65 | 3.75 |
| PLEDGET X | 3.16 | 4.36 |
| PEARL 1 | 2.64 | 3.04 |
| PEARL 2 | 1.93 | 3.08 |
| TAMPAX ORIGINAL 1 | 1.18 | 1.53 |
| TAMPAX ORIGINAL 2 | 1.26 | 1.34 |
| KOTEX | 1.66 | 1.65 |
| OB | 1.89 | 3.11 |
| LIL-LETS | 2.16 | 3.96 |

TABLE 3

Displacement Rates.
Displacement Rates (milliliters/min)

| Product Brand | Absorbency | |
| --- | --- | --- |
| | Regular | Super |
| GENTLE GLIDE | 0.3938 | 0.4715 |
| GENTLE GLIDE 2 | 0.5055 | 0.5918 |
| GENTLE GLIDE Odor Absorbent | 0.4691 | 0.6093 |
| BEYOND | 0.3146 | 0.5334 |
| PLEDGET X | 0.6540 | 0.7694 |
| PEARL 1 | 0.4600 | 0.4004 |
| PEARL 2 | 0.4208 | 0.5303 |
| TAMPAX ORIGINAL 1 | 0.1518 | 0.1587 |
| TAMPAX ORIGINAL 2 | 0.3076 | 0.2458 |
| KOTEX | 0.2325 | 0.2061 |
| OB | 0.3048 | 0.4021 |
| LIL-LETS | 0.3278 | 0.5055 |

TABLE 4

Pledget Weights.
Pledget Weight

| Product Brand | Absorbency | |
| --- | --- | --- |
| | Regular | Super |
| GENTLE GLIDE | 1.87 | 2.93 |
| GENTLE GLIDE 2 | 1.75 | 2.63 |
| GENTLE GLIDE 3 | — | — |
| GENTLE GLIDE Odor Absorbent | 1.79 | 2.82 |
| BEYOND | 1.77 | 2.97 |
| PLEDGET X | 1.94 | 2.70 |
| PEARL 1 | 2.12 | 2.85 |
| PEARL 2 | 2.16 | 2.79 |
| TAMPAX ORIGINAL 1 | 2.07 | 2.84 |
| TAMPAX ORIGINAL 2 | 2.00 | 2.92 |
| KOTEX | 2.40 | 3.26 |
| OB | 1.89 | 2.72 |
| LIL-LETS | 2.10 | 2.77 |

As illustrated in Tables 2 and 3, the inventive tampon 100 (e.g., Pledget X) is seen to provide a higher maximum displacement volume (ml) and rate of displacement (ml/min), as compared to conventional tampon pledgets.

Figure 4A:
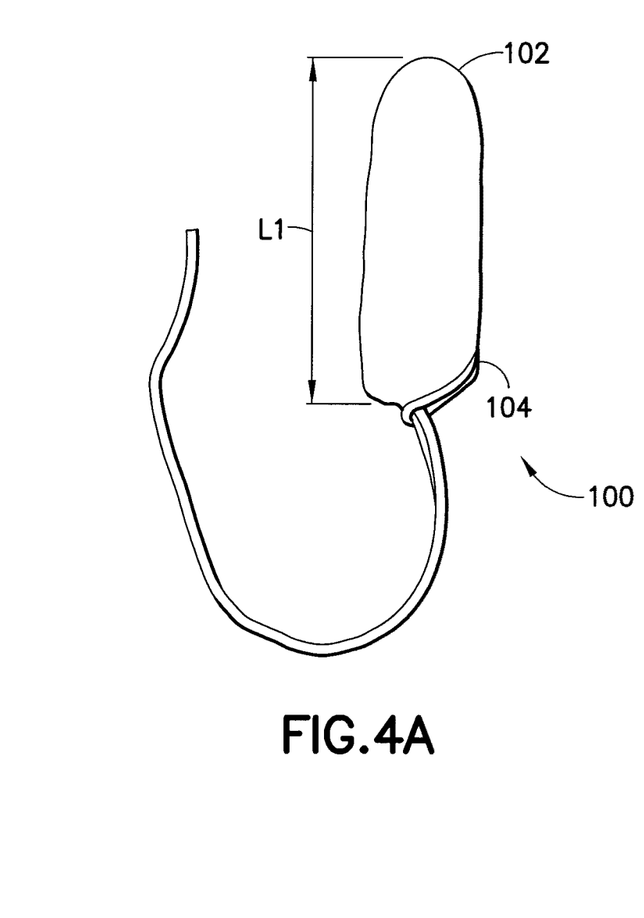
FIGS. 4A and 4B illustrate a side-by-side comparison of the formed tampon pledget of the present invention and a conventional tampon pledget prior to performance testing.
Figure 4B:
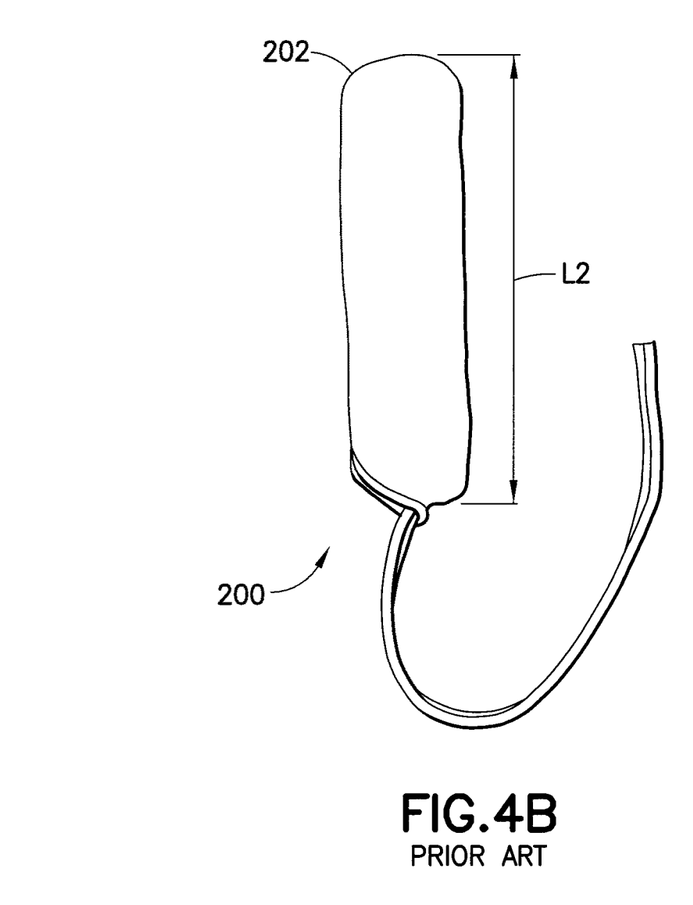
Figure 5A:
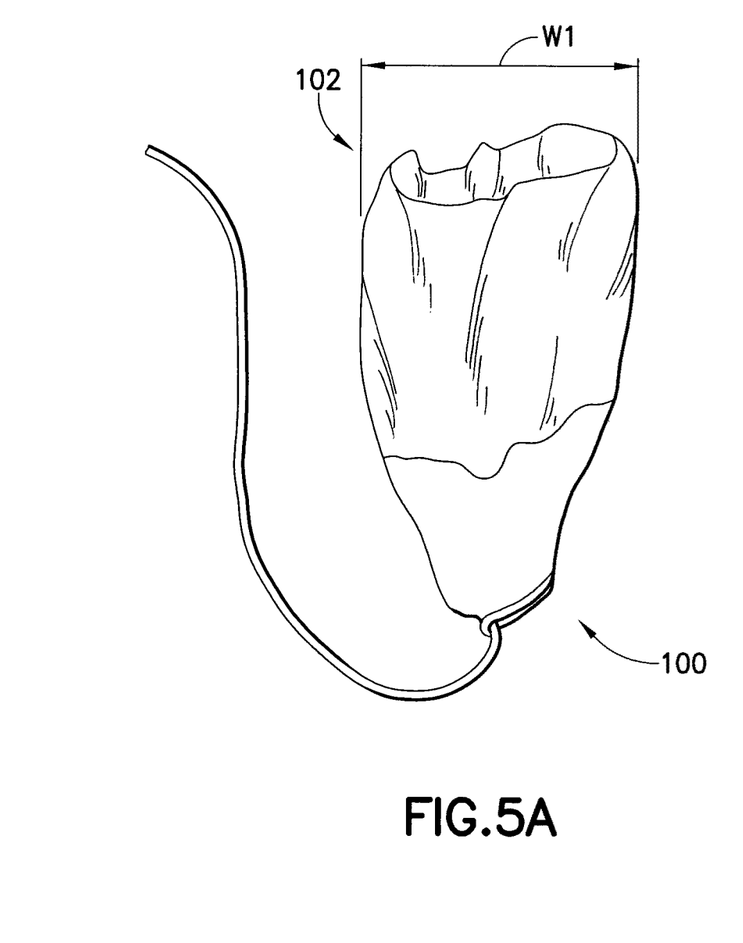
FIGS. 5A and 5B illustrate a side-by-side comparison of the tampon pledgets of FIGS. 4A and 4B after a first performance test.
Figure 5B:
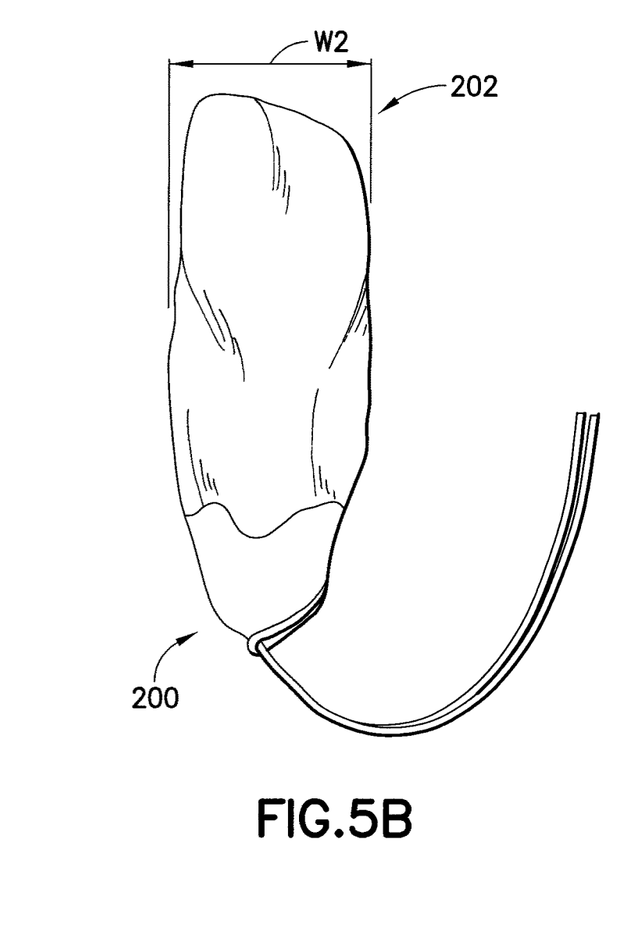

Additionally, the inventive tampon pledget 100 and conventional tampon pledgets were tested using a syngyna absorbency test. FIGS. 4A and 4B provide a side-by-side comparison of the inventive tampon pledget 100 and a conventional GENTLE GLIDE pledget 200 before syngyna testing. As shown in FIGS. 4A and 4B, the inventive tampon pledget 100 is significantly shorter in an overall length dimension (e.g., L1 is less than L2). FIGS. 5A and 5B depict the tampon pledget 100 and GENTLE GLIDE tampon 200 after three (3)

minutes of syngyna testing where fluid is fed to contact a top portion 102 and 202, respectively, of the tampon pledgets 100 and 200. As shown, the inventive tampon pledget 100 is seen to provide a substantial improvement in blooming and, in particular, expansion in its width (e.g., W1 is greater than W2). For example, representative test data of Blooming dimensions in two absorbency types is provided in Table 5.

TABLE 5

Blooming Dimensions.

| "Regular" Absorbency | | | | | | "Super" Absorbency | | | | | |
|---|---|---|---|---|---|---|---|---|---|---|---|
| Conventional Tampon | | | Pledget X | | | Conventional Tampon | | | Pledget X | | |
| W1 (mm) | W2 (mm) | % Chg | W1 (mm) | W2 (mm) | % Chg | W1 (mm) | W2 (mm) | % Chg | W1 (mm) | W2 (mm) | % Chg |
| 13.0 | 18.99 | 46 | 10 | 20.44 | 104 | 15.0 | 24.18 | 61 | 13.0 | 23.04 | 77 |

Figure 6A:
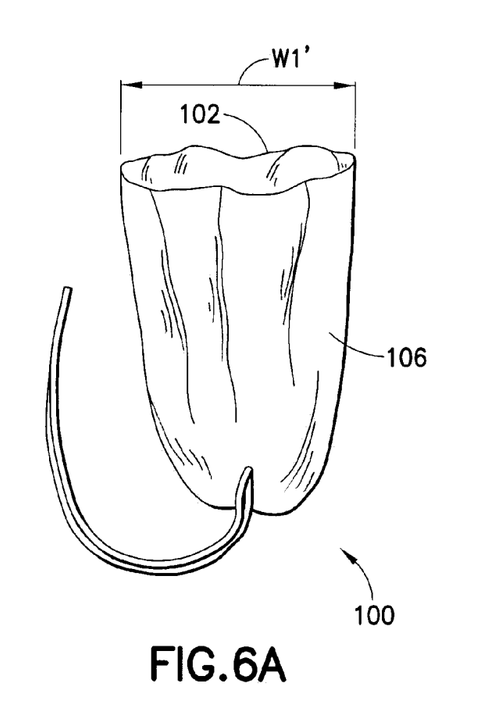
FIGS. 6A and 6B illustrate a side-by-side comparison of the tampon pledgets of FIGS. 4A and 4B after a further performance test.
Figure 6B:
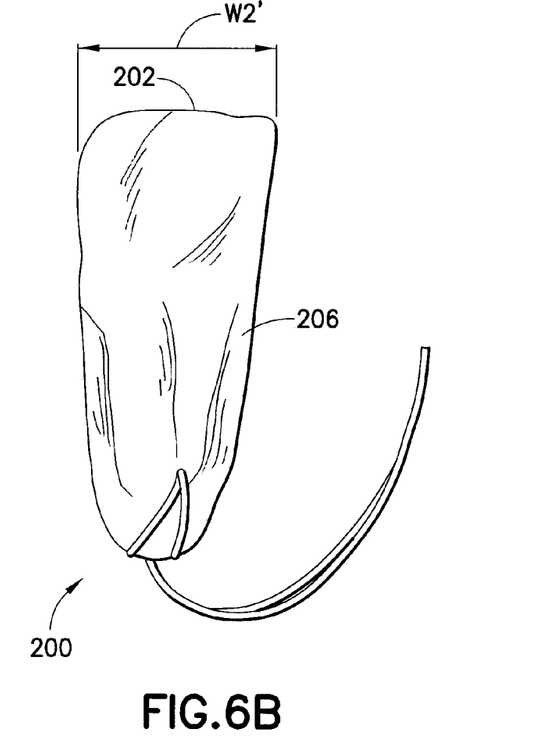

FIGS. 6A and 6B depict the tampon pledget 100 and GENTLE GLIDE tampon 200 after three (3) minutes of syngyna testing where fluid is fed to contact a middle portion 106 and 206, respectively, of the tampon pledgets 100 and 200. As shown, the inventive tampon pledget 100 is again seen to provide a substantial improvement in blooming in its width (e.g., W1' is greater than W2').

MRI scans were also used to investigate tampon pledget performance in female test subjects. The MRI scans confirmed laboratory test results (e.g., the Syngyna and Positive Displacement tests) where the inventive tampon pledget 100 provided a significantly improved expansion in its width as compared to conventional tampon pledgets.

As described above, actual and laboratory tests demonstrate a number of improvements achieved by the inventive, highly compressed tampon pledget 100. For example, some improvements are seen in the following areas.

1. Higher Density:
Pledget X Regular: density measured at 0.4603 g/cc, while a next highest density for a conventional tampon pledget (sold under the BEYOND brand of Regular absorbency) is 0.4070 g/cc.
Pledget X Super: density measured at 0.4755 g/cc, while a next highest density for a conventional GENTLE GLIDE Super absorbency tampon pledget is 0.3829 g/cc.

2. Higher Positive Displacement Results:
Pledget X Regular: maximum displacement volume measured at 3.16 ml, while a next highest maximum displacement volume for the PEARL brand of Regular absorbency tampon pledget is 2.64 ml. Pledget X Regular: rate of displacement is measured at 0.6540, while a next highest rate of displacement for the conventional GENTLE GLIDE Regular absorbency tampon pledget was 0.5055

Pledget X Super: maximum displacement volume measured at 4.36 ml, while a next highest positive displacement volume for a LIL-LETS tampon pledget is measured at 3.96 ml.

Pledget X Super: rate of displacement is measured at 0.7694, while a next highest rate of displacement for a conventional GENTLE GLIDE Super absorbency, odor absorbent tampon pledget was 0.6093.

3. Higher Pledget Expansion in Width Direction
Pledget X Super: expansion to seventy-seven percent (77%) of its original width versus a sixty-one percent (61%) expansion in a width of a conventional GENTLE GLIDE Super absorbency tampon pledget.

In summary, the inventive tampon is seen to provide one or more of the following improvements over conventional tampon pledget:
Density:
Regular absorbency: 0.42 g/cc or greater,
Super absorbency: 0.40 g/cc or greater;
Maximum displacement volume:
Regular absorbency: 2.80 ml or greater,
Super absorbency: 4.20 ml or greater;
Rate of displacement:
Regular absorbency: 0.55 ml/min or greater,
Super absorbency: 0.65 ml/min or greater;
Pledget width/blooming:
Super absorbency: 75% increase or more,
Regular absorbency: 90% increase or more.

Figure 7:
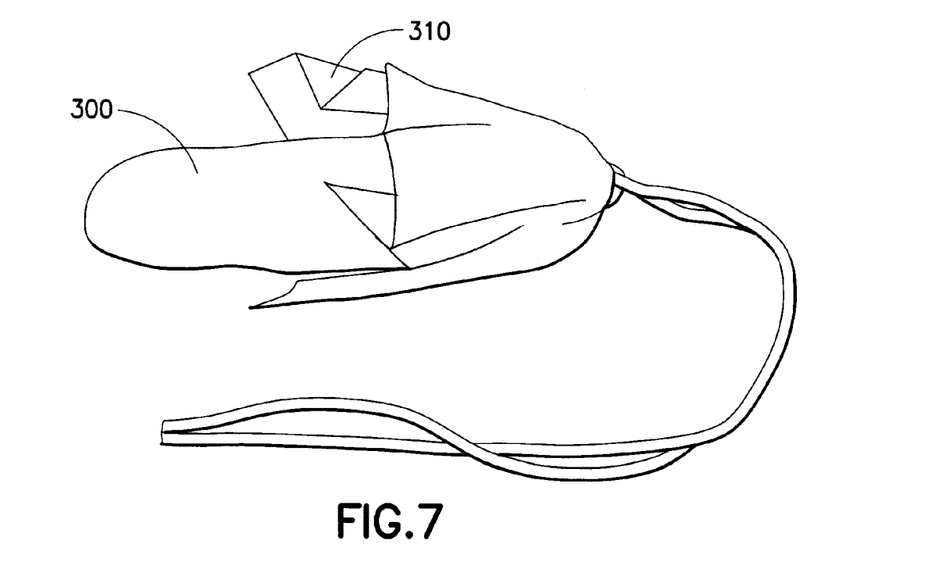
FIG. 7 is a plan view of a formed tampon pledget in accordance with another embodiment of the present invention.

In one embodiment of the present invention, illustrated in FIG. 7, a tampon pledget 300 is provided having the same improved density, displacement volume, rate of displacement, and pledget blooming features as the tampon pledget 100. For even further improvements in leakage protection, the tampon pledget 300 includes an anti-leak shield 310. The anti-leak shield 310 assists by providing by-pass leakage protection during an initial period of expansion to prevent menstrual fluid from flowing around the tampon pledget 300 before the higher density pledget has an opportunity to achieve its desired point of maximum blooming.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of the appended claims.

What is claimed is:
1. A tampon pledget, comprising:
a first pad having a length and a width; and
a second pad having a length and a width,
wherein said first pad is placed perpendicular to said second pad thereby forming a cross configuration said pads being radially and then axially compressed into a generally cylindrical form, wherein after compression, the cylindrical form has an absorbent capacity as measured by the syngyna test of between about 6.0 grams to 9.0 grams, and a density of about 0.4603 grams/cubic centimeter, and at least one of a maximum displacement volume exceeding about 3.00 milliliters, and a rate of displacement exceeding about 0.55 milliliters per minute; and wherein said tampon pledget blooms in a radial direction when it absorbs fluid such that it blooms to an increase of 90% or more.

2. The tampon pledget of claim 1, further comprising a leak shield covering at least a portion of the tampon pledget and having a second absorbency, the second absorbency being less than an absorbency of the tampon pledget, the leak shield comprising a nonwoven material that directs fluid to the tampon pledget when the tampon pledget is inserted in a vaginal cavity of a wearer.

3. The tampon pledget of claim 1, wherein said cylindrical form has a first end geometry that is blunt, conical, tapered, curved, an inverse thereof and/or combinations thereof.

4. The tampon pledget of claim 1, wherein said cylindrical form further comprises a withdrawal string.

5. A tampon pledget, comprising:
a first pad having a length and a width; and
a second pad having a length and a width,
wherein said first pad is placed perpendicular to said second pad thereby forming a cross configuration said pads being radially and then axially compressed into a generally cylindrical form, wherein after compression, the cylindrical form has an absorbent capacity as measured by the syngyna test of between about 9.0 grams to 12.0 grams, and a density of about 0.4755 grams/cubic centimeter, and at least one of a maximum displacement volume exceeding about 4.20 milliliters, and a rate of displacement of exceeding about 0.65 milliliters per minute; and
wherein said tampon pledget blooms in a radial direction when it absorbs fluid such that it blooms to an increase of 75% or more.

6. The tampon pledget of claim 5, further comprising a leak shield covering at least a portion of the tampon pledget and having a second absorbency, the second absorbency being less than an absorbency of the tampon pledget, the leak shield comprising a nonwoven material that directs fluid to the tampon pledget when the tampon pledget is inserted in a vaginal cavity of a wearer.

7. The tampon pledget of claim 5, wherein said cylindrical form has a second end geometry that is blunt, conical, tapered, curved, an inverse thereof and/or combinations thereof.

8. The tampon pledget of claim 5, wherein said cylindrical form further comprises a withdrawal string.

9. A tampon pledget, comprising:
a first pad having a length and a width; and
a second pad having a length and a width,
wherein said first pad is placed perpendicular to said second pad thereby forming a cross configuration said pads being radially and then axially compressed into a generally cylindrical form, wherein after compression, the cylindrical form has an a density of greater than or equal to 0.4603 grams/cubic centimeter, and at least one of a maximum displacement volume exceeding about 3.00 milliliters, and a rate of displacement exceeding about 0.55 milliliters per minute; and
wherein said tampon pledget blooms in a radial direction when it absorbs fluid such that it blooms to an increase of 75% or more.

10. The tampon pledget of claim 9, further comprising a leak shield covering at least a portion of the tampon pledget and having a second absorbency, the second absorbency being less than an absorbency of the tampon pledget, the leak shield comprising a nonwoven material that directs fluid to the tampon pledget when the tampon pledget is inserted in a vaginal cavity of a wearer.

11. The tampon pledget of claim 9, wherein said cylindrical form has a second end geometry that is blunt, conical, tapered, curved, an inverse thereof and/or combinations thereof.

12. The tampon pledget of claim 9, wherein said cylindrical form further comprises a withdrawal string.

13. A tampon pledget, comprising:
a first pad having a length and a width; and
a second pad having a length and a width,
wherein said first pad is placed perpendicular to said second pad thereby forming a cross configuration, said pads being radially and then axially compressed into a generally cylindrical form having a shaped insertion end and a removal end, wherein after compression, the cylindrical form has a density greater than or equal to about 0.42 grams/cubic centimeter, and at least one of a maximum displacement volume exceeding about 3.00 milliliters and a rate of displacement exceeding about 0.55 milliliters per minute; and
wherein said tampon pledget blooms in a radial direction when it absorbs fluid such that it blooms to an increase exceeding 61%.

14. The tampon pledget according to claim 13, wherein at least one of said length and said width of said first pad and said second pad are substantially equal.

15. The tampon pledget according to claim 13, wherein said length of said first pad is about 4 inches.

16. The tampon pledget according to claim 13, wherein said width of said first pad is about 2 inches.

17. The tampon pledget according to claim 13, wherein said length of said second pad is about 4 inches.

18. The tampon pledget according to claim 13, wherein said width of said second pad is about 2 inches.

19. The tampon pledget according to claim 13, wherein said shaped insertion end is a semi-circle, conical, tapered, an oval, an inverted semi-circle, an inverted conical, an inverted taper, or an inverted oval.

20. The tampon pledget according to claim 13, wherein said blunt removal end is blunt or flat.

21. The tampon pledget according to claim 13, wherein said cylindrical form further comprises a withdrawal string.

22. The tampon pledget of claim 13, further comprising a leak shield covering at least a portion of the tampon pledget and having a second absorbency, the second absorbency being less than an absorbency of the tampon pledget, the leak shield comprising a nonwoven material that directs fluid to the tampon pledget when the tampon pledget is inserted in a vaginal cavity of a wearer.

23. The tampon pledget according to claim 13, wherein said tampon pledget has an absorbent capacity of about 6.0 grams to about 9.0 grams.

24. The tampon pledget according to claim 13, wherein said tampon pledget has an absorbent capacity of about 9.0 grams to about 12.0 grams.

* * * * *